(12) United States Patent
Reiffel

(10) Patent No.: US 6,250,800 B1
(45) Date of Patent: Jun. 26, 2001

(54) X-RAY IMAGED IMPLANTED THERMOMETERS

(76) Inventor: Leonard Reiffel, 602 Demming Pl., Chicago, IL (US) 60614

( * ) Notice: Subject to any disclaimer, the term of this patent is extended or adjusted under 35 U.S.C. 154(b) by 0 days.

(21) Appl. No.: 09/681,012

(22) Filed: Nov. 17, 2000

Related U.S. Application Data

(63) Continuation-in-part of application No. 09/218,792, filed on Dec. 21, 1998, now abandoned.
(60) Provisional application No. 60/070,399, filed on Jan. 5, 1998.

(51) Int. Cl.[7] .................................................. G01K 3/06
(52) U.S. Cl. ........................ 374/137; 374/120; 374/190; 374/201; 600/426; 600/427
(58) Field of Search ................................ 374/190, 191, 374/201, 195, 196, 187, 188, 135, 120, 137; 600/426, 427, 407, 429, 437

(56) References Cited

U.S. PATENT DOCUMENTS

| | | | |
|---|---|---|---|
| 1,199,121 | * 9/1916 | Siebert | 374/190 |
| 3,548,308 | 12/1970 | Seabury | 374/190 |
| 3,631,721 | * 1/1972 | Nollen et al. | 374/190 |
| 3,893,111 | * 7/1975 | Cotter | 600/407 |
| 4,138,998 | 2/1979 | Nowogrodzki | 600/430 |
| 4,469,451 | * 9/1984 | Kunetka et al. | 374/137 |
| 4,561,054 | * 12/1985 | Andrews et al. | 600/407 |
| 4,613,757 | * 9/1986 | Deserno et al. | 250/458.1 |
| 4,947,247 | * 8/1990 | Farver | 348/160 |
| 5,109,853 | 5/1992 | Taicher | 600/412 |
| 5,285,785 | * 2/1994 | Meyer | 600/426 |
| 5,394,457 | * 2/1995 | Leibinger et al. | 600/426 |
| 5,396,889 | * 3/1995 | Ueda et al. | 600/407 |
| 5,967,982 | * 10/1999 | Barnett | 600/426 |
| 5,983,123 | * 11/1999 | Shmulewitz | 600/407 |
| 6,097,994 | * 8/2000 | Navab et al. | 600/426 |

FOREIGN PATENT DOCUMENTS

| | | |
|---|---|---|
| 3335129 | 4/1985 | (DE). |
| 0672384 | 9/1995 | (EP). |
| 54-130079 | 10/1979 | (JP). |
| 58-17326 | 2/1983 | (JP). |
| 58-169040 | 10/1983 | (JP). |
| 04164212 | 10/1990 | (JP). |

* cited by examiner

*Primary Examiner*—Diego Gutierrez
*Assistant Examiner*—Stanley J. Pruchnic, Jr.
(74) *Attorney, Agent, or Firm*—Don Moyer

(57) ABSTRACT

Expanding fluid thermometers are implanted in a body—for example in and adjacent to a cancerous tumor—and are read by x-ray imaging.

7 Claims, 2 Drawing Sheets

X-RAY IMAGED IMPLANTED THERMOMETERS

CROSS REFERENCE TO RELATED APPLICATIONS

This application is a continuation in part of U.S. patent application Ser. No. 09/218,792 filed Dec. 21, 1998, now abandoned, which claims benefit of U.S. Provisional Application No. 60/070,399 filed Jan. 5, 1998.

DETAILED DESCRIPTION

The invention—especially useful in cancer therapy—comprises implanted thermometers having a fluid moving from a bulb along a channel to a fluid length, the fluid length—thus the temperature of the bulb—being determined by x-ray imaging.

The invention provides progress over prior art as shown for example in U.S. Pat. Nos. 1,199,121 by Siebert, 3,548,308 by Seabury, 3,893,111 by Cotter, 4,138,998 by Nowogrodzki, 4,561,054 by Andrews, 4,613,757 by Deserno, 4,947,247 by Farver, 5,109,853 by Taicher, 5,983,123 by Shmulewitz, and in Japanese patent documents 58-17326 by Konishi and 58-169040 by Nakada.

Figure 1:
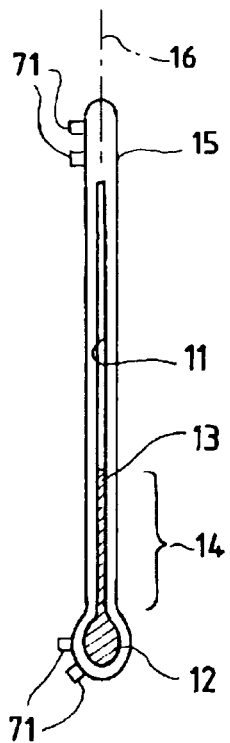
FIG. 1 shows a thermometer cross section.
Figure 2:
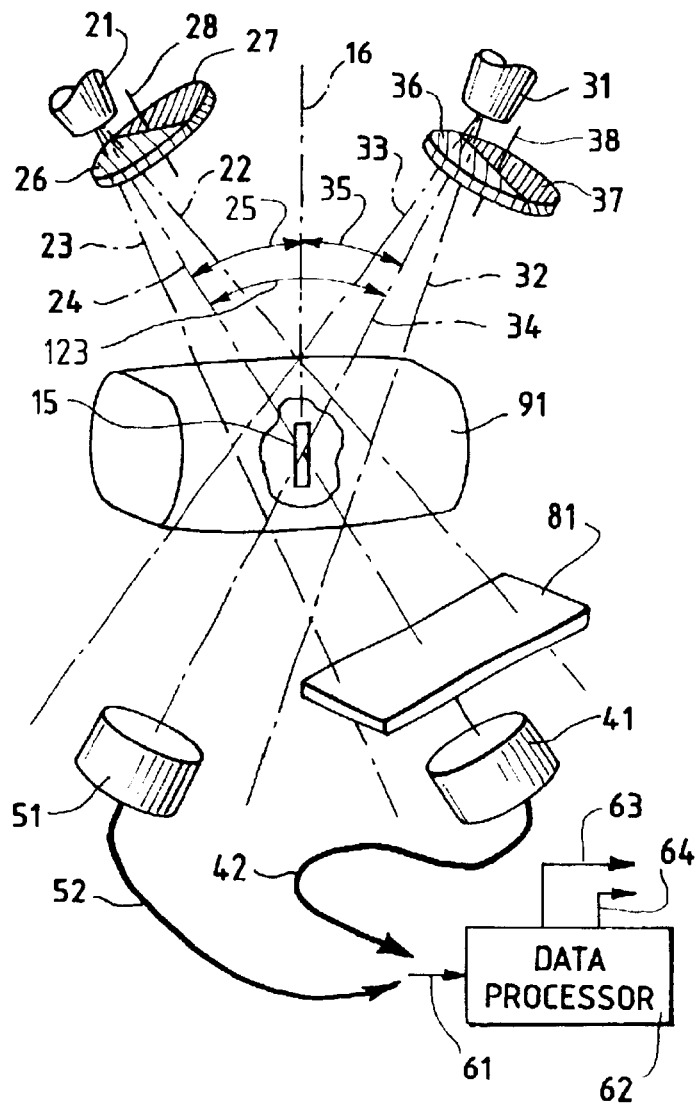
FIG. 2 shows a thermometer in a body imaged by x-radiation.
Figure 3:
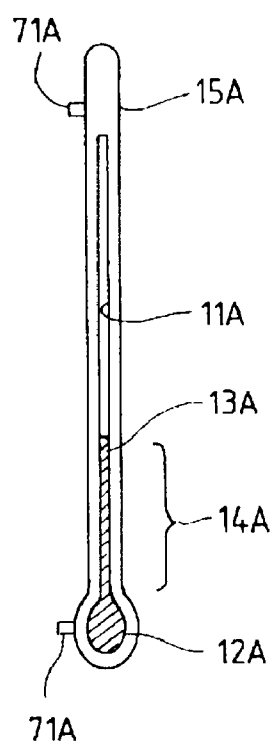
FIG. 3 shows a second thermometer cross section.

The product comprises an imager 41 which images x-radiation, a source 21 which provides an x-radiation beam which overlaps the imager, and a plurality of thermometers implanted in a body 91 from where they can not be imaged by visible light.

Any first thermometer 15 from the plurality of thermometers comprises a first channel 11 and a first bulb 12 terminating the first channel. The first channel and the first bulb enclose a first fluid 13. The first fluid moves along the first channel to a first fluid length 14 which is functionally related to a first bulb temperature.

A first fluid image length of the first fluid length is projected outside the body by the beam and is imaged by the imager.

Fixed first markers 71 are fixed relative to the first channel. A first markers image is projected outside the body by the beam and imaged by the imager. The first markers provide a first calibration length. A first calibration image length of the first calibration length is projected outside the body by the beam and imaged by the imager. A first ratio of the first fluid image length to the first calibration image length is functionally related to the first bulb temperature.

Any second thermometer 15A from the plurality of thermometers comprises a second channel 11A and a second bulb 12A terminating the second channel. The second channel and the second bulb enclose a second fluid 13A. The second fluid moves along the second channel to a second fluid length 14A which is functionally related to a second bulb temperature.

The second thermometer has fixed second markers 71A fixed relative to the second channel. A second markers image projected outside the body by the beam and imaged by the imager is distinct from the first markers image independently of the relative positions and orientations of the first thermometer and the second thermometer.

The second markers provide a second calibration length. A second calibration image length of the second calibration length is projected outside the body by the beam and imaged by the imager. A second ratio of the second fluid image length to the second calibration image length is functionally related to the second bulb temperature.

Markers can take various forms—such as imbedded grains and bands encircling the channel—other than the protrusions depicted. For any thermometer from the plurality of thermometers at least some markers can be provided by bulb dimensions and shapes.

The imager can comprise a first imager component 41 and a second imager component 51. Here the source comprises a first source component 21 and a second source component 31. The first source component provides a first beam component—bounded by vectors 22 and 23—which overlaps the first imager component. The second source component provides a second beam component—bounded by vectors 32, 33—which overlaps the second imager component.

A first central ray 24 of the first beam component makes a non-zero angle 25 with the long axis 16 of the first thermometer. A second central ray 34 of the second beam component makes a non-zero angle 35 with the long axis. The first central ray of the first beam component makes a non-zero angle 123 with a second central ray of the second beam component.

Here the fluid image length comprises a first fluid image length component imaged by the first imager component, paired with a second fluid image length component imaged by the second imager component. The calibration image length comprises a first calibration image length component imaged by the first imager component paired with a second calibration image length component, imaged by the second imager component. The paired image components can be used to determine the location and orientation of a thermometer relative to three orthogonal space coordinates.

Paired source, beam, imager, and image components can be obtained using only the first source 21 and the first imager 41 as shown to obtain first members of paired image components and then moving the first source to a second position, such as the position shown for the second source 31, and moving the first imager to a corresponding second position such as the position of the second imager 51 to obtain second members of the paired image components.

The imager can comprise a large field imager 81, a large field image of the first bulb imaged by the large field imager, and a narrow field x-ray imager 41. The narrow field x-ray imager is positioned with use of the large field image to image the first fluid length.

Figure 4:
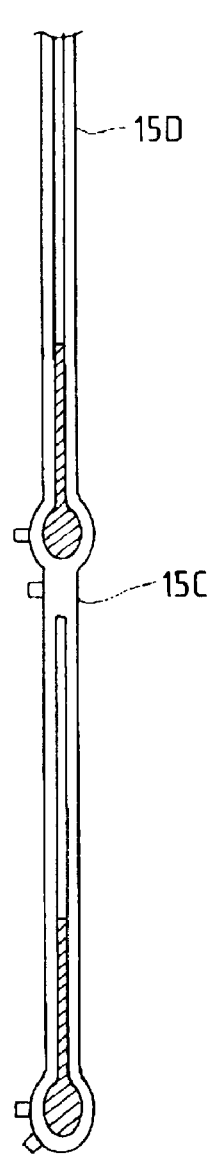
FIG. 4 shows two thermometers connected.

A first thermometer from the plurality of thermometers—15C in FIG. 4—can be connected to a second thermometer from the plurality of thermometers 15D end-to-end with the second bulb distal the first bulb. A string of many thermometers from the plurality can be connected end-to-end.

Figure 5:
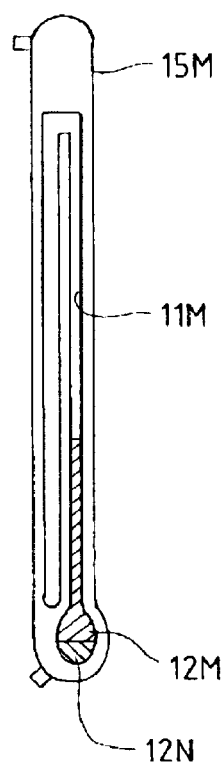
FIG. 5 shows a thermometer with two fluid components.

A thermometer—15M—in FIG. 5—can have a first fluid component 12M and a second fluid component 12N, with the second fluid component moving the first fluid component along the channel 11M and with the first component providing higher x-radiation attenuation than the second component.

The x-radiation can have a peak intensity at an energy which matches an x-radiation absorption edge energy of the fluid. Materials can be used in the imager which are especially sensitive to the energy of an x-radiation absorption edge of the fluid The source and the fluid can be chosen so that there is a peak in the x-ray intensity at an x-radiation absorption edge of the fluid. A filter with an x-radiation absorption edge near an x-ray absorption edge of the fluid can be used, and images made with and without this filter can be compared to enhance the image of the fluid. The x-radiation can be modulated.

The x-radiation can be modulated by alternately passing through a first filter 26, 36 having a first x-radiation absorption edge just below an x-radiation absorption edge of the fluid and a second filter 27, 37 having a second x-radiation absorption edge just above the x-radiation absorption edge of the fluid. This can be done, for example, by rotating the filters 26, 36 and 27, 37 about a modulator axis 28, 38 in front of the source. Then, areas in a series of images which have maximum change in intensity from one image to the next image are images of a fluid length which can be compared to compensate for motion between images and can be contrast enhanced.

Filters and modulation rates used with the second source can be the same as filters used with the first source and alternatively can be different from filters and modulation rates used with the first source thus providing a large number of images to be data processed to enhance the sensitivity and reliability of the reader. A no-filter component can be added to the first beam modulation, to the second beam modulation, and to both.

Dimensions of an example thermometer which can be implanted in a living body by biopsy techniques, are: length of thermometer 20 mm; channel inside diameter 50 microns; bulb length 5 mm; bulb inside diameter 0.75 mm; bulb outside diameter 1.25 mm; thermometer outside diameter away from bulb 90 microns.

A suitable fluid in a thermometer with these dimensions will expand along the channel at about 1 mm per degree Celsius. Thus, for example, if an accuracy of 0.3 Celsius degrees is required, then the fluid length must be measured to an accuracy of 0.3 mm. This sensitivity is that sought in hyperthermia treatments of cancerous tumors. Smaller and larger thermometers can be made as needed for specific applications with more or less stringent requirements for size and sensitivity.

The preferred form of the imager is a high resolution imager, such as a microchannel plate detector, which feeds a transducer, such as a CCD video camera, which produces an imager output signal 42, 52 which is input 61 to a data processor 62 which then produces an output signal 63.

The output signal can indicate the temperature of the bulb using various visual, audible, and tactile means. The output signal can also have a component 64 which controls a process in the body.

The output, of a microchannel imager for example, can be viewed directly, in which case this is the output signal. Other x-radiation detectors can be used including detectors which produce a digital output directly.

Any first thermometer from the plurality of thermometers has a first thermal calibration which relates the first fluid length to the first temperature of the first bulb and has a first calibration length provided by the first markers. Any second thermometer from the plurality of thermometers has a second thermal calibration which relates the second fluid length to the second temperature of the second bulb and has a second calibration length provided by the second markers.

Because the first markers image is distinct from the second markers image independently of positions and orientations of thermometers in the beam, the first thermal calibration and the first calibration length can be associated with the first fluid image length and first calibration image length and the second thermal calibration and the second calibration length can be associated with the second fluid image length and second calibration image length.

The position of the first thermometer along the beam can be determined from paired image components and by comparing the first bulb diameter with the first bulb image diameter. The orientation of the first thermometer relative to the beam can be determined from paired image components and by comparing the first calibration length with the first calibration image length.

Geometric factors—the distance from the source to the imager, and the position and orientation of the first thermometer along the beam—are then used to determine the fluid length from the fluid image length. From this the first thermal calibration is used to determine the temperature of the bulb.

A thermometer can have a channel with a varying diameter along the channel so that the sensitivity of the thermometer varies accordingly along the channel to have maximum sensitivity around a critical temperature.

While the specific examples of thermometer, source, and imager described above are especially well adapted for thermometers implanted in living tissue, these and other examples consistent with the principles of the invention can be used in various bodies. Parallel imaging arrangements using other wavelengths of electromagnetic radiation and using acoustic radiation can be substituted in appropriate conditions. Parallel forms for the calibration techniques, positioning techniques, and image enhancement techniques can be used with these parallel imaging arrangements.

What is claimed is:

1. Implanted thermometers and reader product, comprising:

1) an imager which images x-radiation;
   2) a source which provides an x-radiation beam overlapping the imager; and
   3) a plurality of thermometers implanted in a body from where they can not be imaged by visible light, any first thermometer from the plurality of thermometers comprising:

3.1) a first channel and a first bulb terminating the first channel, the first channel and the first bulb enclosing a first fluid, the first fluid moving along the first channel to a first fluid length functionally related to a first bulb temperature, a first fluid image length of the first fluid length being projected outside the body by the beam and imaged by the imager; and 3.2) fixed first markers with a first markers image being projected outside the body by the beam and imaged by the imager, the first markers providing a first calibration length, a first calibration image length of the first calibration length being projected outside the body by the beam and imaged by the imager, with a first ratio of the first fluid image length to the first calibration image length being functionally related to the first bulb temperature, where any second thermometer from the plurality of thermometers having fixed second markers with a second markers image projected outside the body by the beam and imaged by the imager being distinct from the first markers image independently of relative positions and orientations of the first thermometer and the second thermometer.

2. The product of claim 1 wherein:
1) the imager comprises a first imager component and a second imager component;
2) the source comprises a first source component and a second source component, with the first source component providing a first beam component overlapping the first imager component, and the second source component providing a second beam component overlapping the second imager component, with a first central ray of the first beam component making a non-zero angle with a second central ray of the second beam component;
3) the fluid image length comprises a first fluid image length component imaged by the first imager component paired with a second fluid image length component imaged by the second imager component; and
4) the calibration image length comprises a first calibration image length component imaged by the first imager component paired with a second calibration image length component imaged by the second imager component.

3. The product of claim 1 wherein the imager comprises:
1) a large field imager,
2) a large field image of the first bulb imaged by the large field imager; and
3) a narrow field x-ray imager, the narrow field x-ray imager being positioned with use of the large field image to image the first fluid length.

4. The product of claim 1 wherein the first thermometer from the plurality of thermometers is connected to a second thermometer from the plurality of thermometers.

5. The product of claim 1 wherein the first fluid has a first fluid component and a second fluid component, with the second fluid component moving the first fluid component along the channel, and with the first fluid component providing higher x-radiation attenuation than the second fluid component.

6. The product of claim 1 wherein the x-radiation has a peak intensity at an energy which matches a fluid x-radiation absorption edge energy.

7. The product of claim 1 wherein the x-radiation is modulated.

* * * * *